(12) United States Patent
Helmer et al.

(10) Patent No.: US 10,065,000 B2
(45) Date of Patent: Sep. 4, 2018

(54) ASSEMBLY FOR A DRUG DELIVERY DEVICE AND DRUG DELIVERY DEVICE

(71) Applicant: SANOFI-AVENTIS DEUTSCHLAND GMBH, Frankfurt am Main (DE)

(72) Inventors: Michael Helmer, Frankfurt am Main (DE); Christian Dexheimer, Langen (DE); Winfried Huthmacher, Frankfurt (DE); Christoph Eissengarthen, Ginsheim (DE); Carsten Mosebach, Mainz (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 255 days.

(21) Appl. No.: 14/391,056

(22) PCT Filed: Apr. 17, 2013

(86) PCT No.: PCT/EP2013/057977
§ 371 (c)(1),
(2) Date: Oct. 7, 2014

(87) PCT Pub. No.: WO2013/156516
PCT Pub. Date: Oct. 24, 2013

(65) Prior Publication Data
US 2015/0119816 A1    Apr. 30, 2015

(30) Foreign Application Priority Data
Apr. 19, 2012 (EP) .................................. 12164682

(51) Int. Cl.
*A61M 5/315* (2006.01)

(52) U.S. Cl.
CPC ...... *A61M 5/31555* (2013.01); *A61M 5/3158* (2013.01); *A61M 5/3157* (2013.01); *A61M 5/31565* (2013.01); *A61M 2205/581* (2013.01)

(58) Field of Classification Search
CPC ............ A61M 5/31555; A61M 5/3158; A61M 2205/581; A61M 5/31548;
(Continued)

(56) References Cited

U.S. PATENT DOCUMENTS

| 533,575 A | 2/1895 | Wilkens |
| 4,466,426 A * | 8/1984 | Blackman ........... A61M 5/3158 600/5 |

(Continued)

FOREIGN PATENT DOCUMENTS

| CA | 2138528 C | 12/1998 |
| CA | 2359375 A1 | 7/2000 |

(Continued)

OTHER PUBLICATIONS

Chinese Office Action for CN Application No. 201380019281.9, dated Jun. 27, 2016.
(Continued)

*Primary Examiner* — Bradley J Osinski
*Assistant Examiner* — Nilay Shah
(74) *Attorney, Agent, or Firm* — Fish & Richardson P.C.

(57) ABSTRACT

An assembly for a drug delivery device is provided, the assembly including a blocking element and a piston rod having an interaction feature adapted and arranged to mechanically cooperate with the blocking element. For delivering a dose of a drug, the piston rod is configured to be moved from an initial position to an end position with respect to the blocking element, wherein the interaction feature is provided along the path between the initial position and the end position. An operating noise is provided to the user when the interaction feature mechanically cooperates with the blocking element while moving the piston rod for dose delivery. The interaction feature is adapted for homogenizing the operating noise so as to prevent the (Continued)

operating noise from being interpreted by the user as signalling the end of the dose delivery operation. Furthermore, a drug delivery device is provided.

16 Claims, 2 Drawing Sheets

(58) Field of Classification Search
CPC .......... A61M 5/31545; A61M 5/31565; A61M 5/3157; A61M 5/31566; A61M 5/31578
See application file for complete search history.

(56) References Cited

U.S. PATENT DOCUMENTS

| | | |
|---|---|---|
| 4,865,591 A | 9/1989 | Sams |
| 5,092,842 A | 3/1992 | Bechtold et al. |
| 5,226,895 A | 7/1993 | Harris |
| 5,226,896 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,807,346 A | 9/1998 | Frezza |
| 5,820,602 A | 10/1998 | Kovelman et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman et al. |
| 6,613,023 B1 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,678,084 B2 | 3/2010 | Judson et al. |
| 7,850,662 B2 | 12/2010 | Veasey et al. |
| 8,187,233 B2 | 5/2012 | Harms et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2005/0222540 A1 | 10/2005 | Kirchhofer et al. |
| 2006/0153693 A1 | 7/2006 | Fiechter et al. |
| 2007/0016143 A1 | 1/2007 | Miller et al. |
| 2009/0275916 A1 | 11/2009 | Harms et al. |
| 2009/0287161 A1* | 11/2009 | Traub ................ A61M 5/31595 604/208 |
| 2010/0105003 A1 | 4/2010 | Weill et al. |
| 2010/0137792 A1* | 6/2010 | Boyd ................ A61M 5/31555 604/68 |
| 2011/0046565 A1 | 2/2011 | Radmer et al. |

FOREIGN PATENT DOCUMENTS

| | | |
|---|---|---|
| CN | 101626795 A | 1/2010 |
| CN | 101674857 A | 3/2010 |
| CN | 101912648 A | 12/2010 |
| CN | 102238972 A | 11/2011 |
| DE | 102007013838 | 9/2008 |
| EP | 0496141 A1 | 7/1992 |
| EP | 0897729 A2 | 2/1999 |
| EP | 0937471 | 8/1999 |
| EP | 0937476 | 8/1999 |
| EP | 1776975 A2 | 4/2007 |
| EP | 2438944 | 4/2012 |
| JP | 2008526325 T | 7/2008 |
| WO | 93/07922 A1 | 4/1993 |
| WO | 93/24160 A1 | 12/1993 |
| WO | 99/38554 | 8/1999 |
| WO | 01/10484 | 2/2001 |
| WO | 02/30495 A2 | 4/2002 |
| WO | 02/030495 A2 | 4/2002 |
| WO | 02/092153 A2 | 11/2002 |
| WO | 03/080160 A1 | 10/2003 |
| WO | 2006/072188 A1 | 7/2006 |
| WO | 2006/084876 A1 | 8/2006 |
| WO | 2008/058666 | 5/2008 |
| WO | 2008/058668 | 5/2008 |
| WO | 2009/092807 A1 | 7/2009 |
| WO | 2010/063707 A1 | 6/2010 |
| WO | 2012/022810 | 2/2012 |

OTHER PUBLICATIONS

Chinese Search Report for CN Application No. 201380019281.9, dated Jun. 17, 2016.
International Search Report for Int. App. No. PCT/EP2013/057977, completed Jul. 2, 2013.
European Search Report for EP App. No. 12164682, dated Oct. 10, 2012.
Japanese Office Action for JP Application No. 2015-506226, dated Feb. 7, 2017.
Chinese Office Action for CN Application No. 201380019281.9, dated Feb. 13, 2017.
Chinese Supplemental Search Report for CN Application No. 201380019281.9, dated Feb. 4, 2017.

* cited by examiner

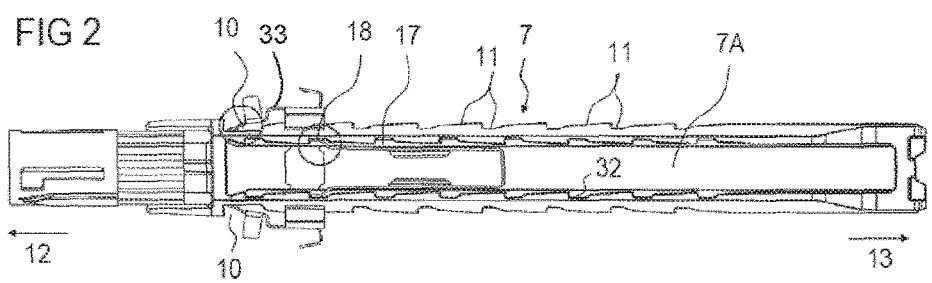
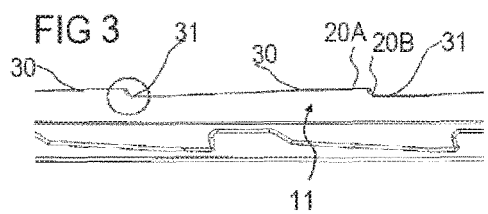
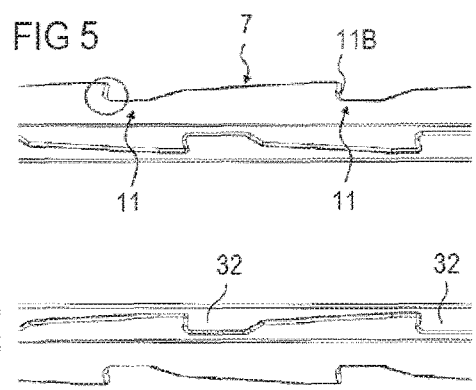
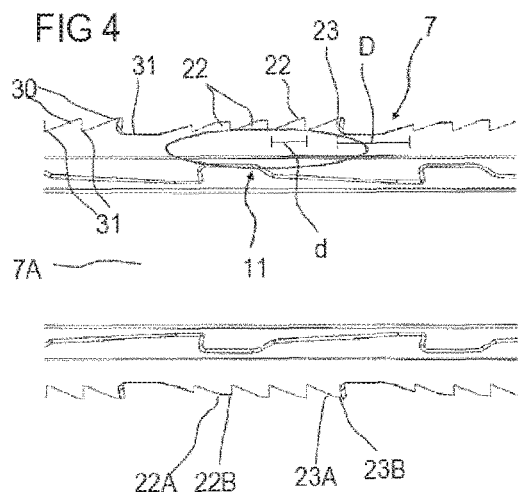

ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2013/057977 filed Apr. 17, 2013, which claims priority to European Patent Application No. 12164682.2 filed Apr. 19, 2012. The entire disclosure contents of these applications are herewith incorporated by reference into the present application.

TECHNICAL FIELD

This disclosure relates to an assembly for a drug delivery device and to a drug delivery device.

BACKGROUND

In a drug delivery device, often, a bung within a reservoir containing a plurality of doses of a drug is displaced by a piston rod. Thereby, a dose of the drug is expelled from the reservoir.

A drug delivery device is described in documents WO 2008/058666 A1 and WO 2008/058668 A1, for example.

SUMMARY

It is an object of the present disclosure to provide an assembly for an improved drug delivery device, e.g. a drug delivery device having increased user safety.

This object may, inter alia, be achieved by the subject matter of the independent claim. Advantageous embodiments and refinements are the subject matter of the dependent claims. However, further advantageous concepts may be disclosed herein besides the ones which are currently claimed.

One aspect relates to an assembly for a drug delivery device. The assembly may comprise a blocking element. The assembly may further comprise a piston rod. The piston rod may have an interaction feature, which may, for example, prevent movement of the piston rod counter an advancing direction in which the piston rod is moved during dose delivery. The interaction feature may be adapted and arranged to mechanically cooperate with the blocking element. For delivering a dose of a drug, preferably a fixed dose of the drug, the piston rod may be arranged and configured to be moved from an initial position to an end position with respect to the blocking element. The interaction feature may be provided along the path between the initial position and the end position. An operating noise may be provided to the user when the interaction feature mechanically cooperates with the blocking element while moving the piston rod from the initial position to the end position for dose delivery. The operating noise may be so loud such that the user can perceive the noise. The operating noise may comprise a tactile component. The operating noise may be rather unwanted as it could be misinterpreted by the user as an intended signal for completion of the delivery operation although it signals only the mechanical cooperation of two or more components of the device during the delivery operation. In particular, the operating noise may be provided before the piston rod is positioned in the end position with respect to the blocking element, i.e. before the dose delivery operation is completed. The interaction feature may be adapted for homogenizing the operating noise. In this way, the operating noise may be prevented from being interpreted by the user as signalling the end of the dose delivery operation.

As the operating noise is provided before the dose delivery operation is completed, a user could misinterpret the operating noise as signalling the end of the delivery operation. The operating noise may be generated, for example, before a dose button of the device, the movement of which is transferred to the piston rod, has reached its end position. If the user misinterpreted the operating noise as signalling the end of the dose delivery operation, the user would likely immediately stop to move the piston rod further towards the end position and, thus, not the complete dose of the drug but only a part of the dose would delivered to the user. This could have fatal consequences for the user.

The interaction feature may be adapted and arranged to prevent that the user stops moving the piston rod towards the end position before the dose delivery operation is completed. In particular, the interaction feature may mechanically cooperate with the blocking element in a way such that the operating noise is minimized, i.e. such that the user does not misinterpret the operating noise as signalling the end of the dose delivery operation. Alternatively or additionally, the interaction feature may mechanically cooperate with the blocking element in a way such that the user may realize multiple operating noise signals during a dose delivery operation of the piston rod. Multiple operating signals which are generated throughout the movement of the piston rod render the operating noise or operating noise less significant. Accordingly, the user will not associate the signals or noises with the end of the dose delivery operation. In this way, the user may perform the delivery operation completely, in particular without interrupting the delivery operation due to an operating noise of high significance during the delivery operation which is mistaken as signalling the end of the delivery operation before this operation has actually been completed. In particular, the user will therefore more reliably move the piston rod with respect to the blocking element until the piston rod has reached its end position with respect to the blocking element. Underdosing may be prevented in this way. This may facilitate provision of a drug delivery device with increased user safety.

The proposed assembly is particularly advantageous for fixed dose devices, e.g. devices with pre-set, non user variable, preferably equal doses. In fixed dose devices the piston rod has to travel a specific distance for delivering the fixed dose. This distance is pre-set. Accordingly, so as compared to variable dose devices where the travel distance of the piston rod corresponds to the size of the dose which was previously set by the user, the noises generated during dose delivery may be tuned more easily so as to render a single noise event less significant for a user.

A further aspect relates to a drug delivery device. The drug delivery device may comprise the previously described assembly. Accordingly, features which are described herein above and below for the assembly may also apply for the device and vice versa.

The device may further comprise a housing. The device may further comprise a reservoir. The reservoir may hold at least one, preferably a plurality of doses of the drug. The at least one blocking element may be integrally formed with or may be connected to the housing. The blocking element may be secured against axial and rotational movement with respect to the housing.

The interaction feature may be configured such that the operating noise created by mechanical cooperation of the interaction feature and the blocking element does not cause the user to interrupt the dose delivery operation before it has been completed. In particular, the operating noise or operating noise may be homogenized, e.g. the significance which a single noise event has on the user perception may be reduced by way of the proposed assembly. The proposed assembly is particularly advantageous for modifying an assembly in which a single operating noise is necessarily generated in each case, for example because the operation of the assembly necessarily involves an operating noise, like the noise which is generated by engagement of a detent. The proposed assembly reduces the significance of the necessary operating noise to the user. This may be achieved, for example by providing elements which generate a plurality of noises, which renders the single noise event less significant, or by reducing the strength of the operating noise, e.g. reducing the noise. In this way, a user-friendly and safe drug delivery device may be provided.

According to a preferred embodiment, an assembly for a drug delivery device is provided, the assembly comprising a blocking element and a piston rod having an interaction feature which is adapted and arranged to mechanically cooperate with the blocking element. For delivering a dose of a drug, the piston rod is arranged and configured to be moved from an initial position to an end position with respect to the blocking element, wherein the interaction feature is provided along the path between the initial position and the end position. An operating noise is provided to the user when the interaction feature mechanically cooperates with the blocking element while moving the piston rod from the initial position to the end position for dose delivery, wherein the interaction feature is adapted for homogenizing the operating noise so as to prevent the operating noise from being interpreted by the user as signalling the end of the dose delivery operation.

According to a preferred embodiment, a drug delivery device is provided comprising the previously described assembly, wherein the device comprises a housing and a reservoir holding a plurality of doses of the drug, wherein the at least one blocking element is integrally formed with or is connected to the housing, and wherein the blocking element is secured against axial and rotational movement with respect to the housing.

Of course, features described above in connection with different aspects and embodiments may be combined with each other and with features described below.

Further features and refinements become apparent from the following description of the exemplary embodiments in connection with the accompanying figures.

BRIEF DESCRIPTION OF THE FIGURES

FIG. 2 schematically shows a sectional side view of the drug delivery device of FIG. 1, FIG. 3 schematically shows a sectional side view of a part of the drug delivery device of FIG. 1, FIG. 4 schematically shows a sectional side view of a part of the drug delivery device of FIG. 1 according to a further embodiment, FIG. 5 schematically shows a sectional side view of a part of a drug delivery device known from the prior art.

Like elements, elements of the same kind and identically acting elements may be provided with the same reference numerals in the figures.

DETAILED DESCRIPTION

Figure 1:
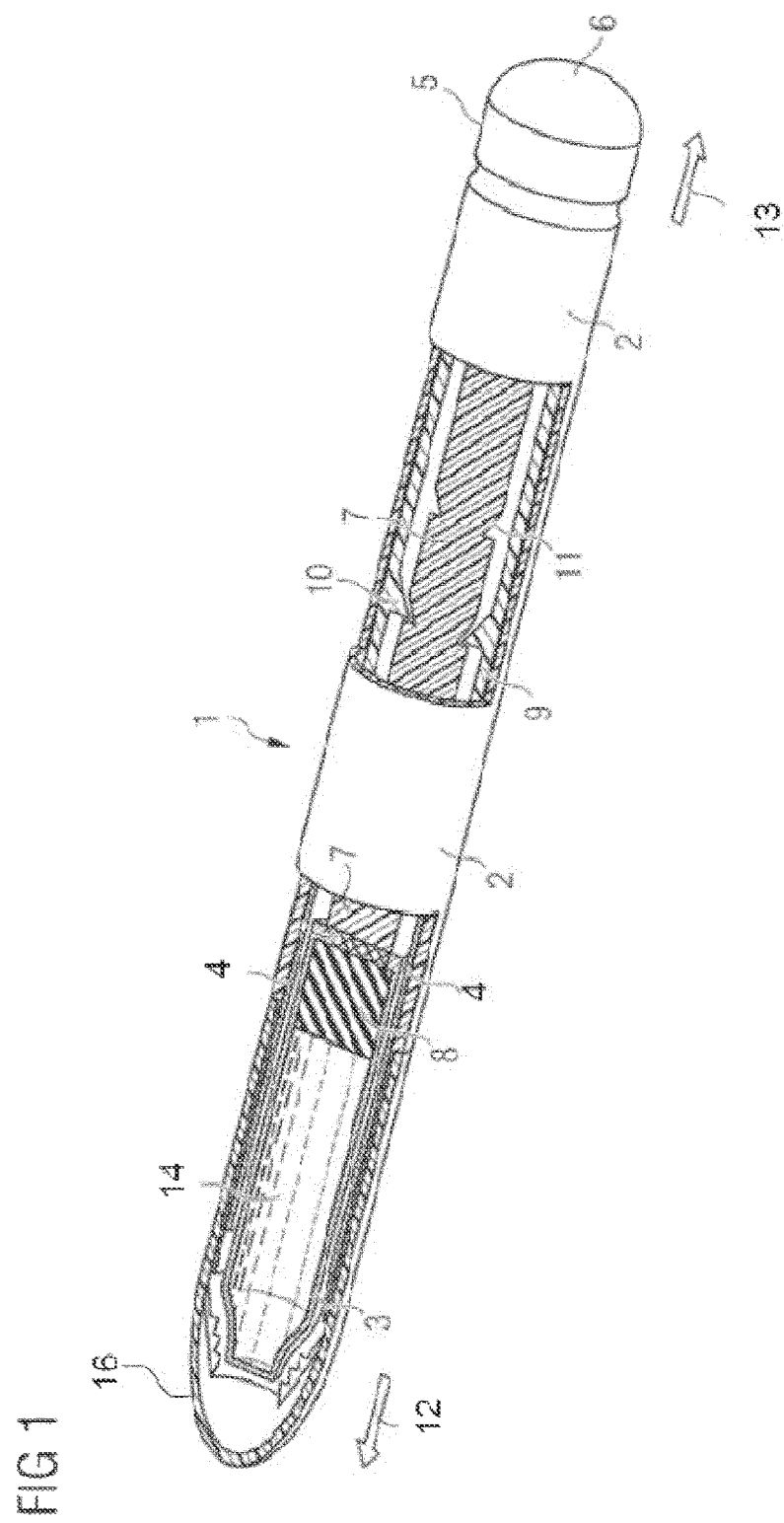
FIG. 1 schematically shows a perspective side view of a drug delivery device.

In FIG. 1 a drug delivery device 1 shown. The drug delivery device 1 comprises a housing 2. The drug delivery device 1 and/or a component thereof have a distal end and a proximal end. The distal end is indicated by arrow 12. The proximal end is indicated by arrow 13. The term "distal end" designates that end of the drug delivery device 1 or a component thereof which is or is to be arranged closest to a dispensing end of the drug delivery device 1. The term "proximal end" designates that end of the system 1 or a component thereof which is or is to be arranged furthest away from the dispensing end of the system 1. The distal end and the proximal end are spaced apart from one another in the direction of an axis. The axis may be the longitudinal axis of the drug delivery device 1 or elements thereof.

The drug delivery device 1 comprises a reservoir 3. The reservoir 3 is retained within a reservoir holder 4. The reservoir holder 4 stabilizes the position of the reservoir 3 mechanically. The reservoir holder 4, in particular the proximal end of the reservoir holder 4, is connectable, e.g. by a threaded engagement, to the housing 2 of the drug delivery device 1. Alternatively, the reservoir 3 may be directly connected to the housing 2 (see, for example, FIG. 1). In this case, the reservoir holder 4 may be redundant.

The reservoir 3 contains a drug 14, preferably a plurality of doses of the drug 14. The drug 14 may be a liquid drug. The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A bung 8 is moveably retained within the reservoir 3. The bung 8 seals the reservoir 3 proximally. Particularly, the reservoir may be a, e.g. pre-filled, cartridge. Movement of the bung 8 in the distal direction with respect to the reservoir 3 causes the drug 14 to be dispensed from the reservoir 3, provided that fluid communication between the distal end of the reservoir 3 and the environment, e.g. via a needle (not explicitly shown in the Figures), is established.

A removable cap 16 is releasably retained over the distal end of the reservoir holder 4.

The drug delivery device 1 may be a pen-type device, in particular a pen-type injector. The device 1 may be configured for dispensing fixed doses of the drug 14, i.e. doses which may not be varied by a user. The device 1 can be a re-usable device, which means that the reservoir 3 can be replaced, in particular during a reset operation, by a replacement reservoir for dispensing a plurality of doses from the replacement reservoir. Alternatively, the device 1 may be a disposable device. In this case, the reservoir 3 may not be replaced. The reservoir may, for example, be non-releasably connected to the reservoir holder 4. The drug delivery device 1 may be a multidose device, i.e. a device configured for setting and dispensing a plurality of doses of the drug 14. The drug delivery device 1 comprises a drive mechanism. The drive mechanism is used for setting and dispensing a dose of the drug 14.

The drive mechanism comprises a piston rod 7. The piston rod 7 has a distal and a proximal end. The distal end of the piston rod 7 may be the end which is closest to the distal end 12 of the drug delivery device 1 when the piston rod 7 has been introduced in the device 1. The proximal end of the piston rod 7 may be the end which is furthest away from the distal end 12 of the drug delivery device 1 when the piston rod 7 has been introduced in the device 1. The piston rod 7 extends through the housing 2 of the device 1. The piston rod 7 is designed to transfer axial movement through the drug delivery device 1, for example for the purpose of delivering the drug 14. The piston rod 7 is axially displaceable in a dose delivery direction for delivering a dose of the drug 14. The dose delivery direction may be the distal direction with respect to the housing 2. Preferably, the piston rod 7 is prevented from being axially displaced in a dose setting direction, which is described later on in detail. The dose setting direction may be the proximal direction with respect to the housing 2. Preferably, the piston rod 7 is prevented from being rotated with respect to the housing 2 when setting and when delivering a dose of the drug 14, for example, by mechanical cooperation with the housing 2. The piston rod 7 comprises an outer structure and an inner structure (see FIG. 2) which are described later on in detail. For clarity reasons, the inner structure of the piston rod 7 is not shown in FIG. 1. The device 1 comprises a screw nut 33 (see FIG. 2). The screw nut 33 is threadedly engaged with the piston rod 7. In particular, the screw nut 33 is screwed to the distal end section of the piston rod 7. By means of the screw nut 33, the length of the piston rod 7 can be varied. In this way, the length of the piston rod 7 can be adjusted such that the piston rod 7 abuts the bung 8 before setting and dispensing a first dose from the device 1. User-operated priming steps for bringing the piston rod 7 and the bung 8 in abutment may be made redundant in this way.

FIG. 2 schematically shows a sectional side view of the drug delivery device of FIG. 1.

The drive mechanism comprises a drive member 17. The drive member 17 is arranged in an interior 7A of the piston rod 7. The drive member 17 is displaced in the dose setting direction with respect to the housing 2 for setting the dose of the drug 14. The drive member 17 is displaced with respect to the piston rod 7 when setting the dose of the drug 14. The drive member 17 is displaced in the dose delivery direction with respect to the housing 2 for delivering the dose of the drug 14. When delivering the dose, movement of the drive member 17 in the distal direction is transferred into movement of the piston rod 7 in the distal direction with respect to the housing 2. The piston rod 7 comprises a set of indentations 32 (see, for example, FIG. 5). The indentations 32 extend longitudinally along an internal surface of the piston rod 7. The drive member 17 comprises at least one flexible arm 18. The indentations 32 mechanically cooperate with the drive member 17, in particular with the flexible arm 18 of the drive member 17 for transferring movement of the drive member 17 in the dose delivery direction to the piston rod 7.

The drive mechanism comprises a dose member 5. The drug delivery device 1 comprises a dose button 6. The dose button 6 may be integrally formed with the dose member 5 or may be connected to the dose member 5. In the latter case the dose button 6 may be secured to the dose member 5, in particular secured against rotational movement with respect to the dose member 5. A user moves the dose member 5 with respect to the housing 2 for setting a dose of the drug 14. This movement causes the drive member 17 to be moved proximally with respect to the piston rod 7. Before setting a dose of the drug 14, the dose button 6 is arranged in a starting position with respect to the housing 3.

The device 1 comprises a blocking element 10. The blocking element 10 protrudes in the radial inward direction from the housing 3. The blocking element 10 may comprise a pawl arm. The blocking element 10 may be flexible. In particular, the blocking element 10 is flexible in the radial direction with respect to the housing 3. The blocking element 10 is secured against axial and rotational movement with respect to the housing 2. The device 1 may comprise a plurality of blocking elements 10. Different blocking elements 10 comprise an equal axial position with respect to the main longitudinal axis of the piston rod 7. The device 1 comprises an inner sleeve 9. The inner sleeve 9 may be an insert sleeve within the housing 2. Preferably, the inner sleeve 9 is secured against rotational and translational movement with respect to the housing 2. The inner sleeve 9 may comprise the blocking element 10. The blocking element 10 protrudes radially inwards from the inner sleeve 9. Alternatively, the blocking element 10 may be part of the housing 2 or may be secured to the housing 2. In this case, the inner sleeve 9 may be redundant.

The piston rod 7 comprises a plurality of interaction features 11. The interaction features 11 extend along an outer surface of the piston rod 7. Succeeding interaction features 11 comprise an equal axial dimension along the outer surface of the piston rod 7, e.g. equal lengths as seen along the direction of movement of the piston rod 7 during dose delivery. This may help enabling provision of a fixed dose drug delivery device 1, for example.

FIG. 3 schematically shows a sectional side view of a part of the drug delivery device of FIG. 1. FIG. 4 schematically shows a sectional side view of a part of the drug delivery device of FIG. 1 according to a further embodiment.

The respective interaction feature 11 comprises at least one indentation 31. The respective interaction feature 11 comprises at least one elevation 30. In other words, the respective interaction feature 11 comprises at least one, e.g. exactly one, pair formed by an elevation 30 and an indentation 31. The elevation 30 protrudes from the outer surface of the piston rod 7 in the radial outward direction. The elevation 30 and the indentation 31 of succeeding interaction features 11 are arranged along the piston rod 7 in an alternating fashion as it is apparent from FIGS. 2, 3 and 4.

The interaction features 11 mechanically cooperate with the blocking element 10. Thereby, only one interaction feature 11 mechanically cooperates with the blocking element 10 during one dose delivery operation, i.e. for delivering a predetermined, thus, fixed dose of the drug 14. For delivering one dose of the drug, the piston rod 7 is moved from an initial position with respect to the blocking element 10 to an end position with respect to the blocking element 10. The respective interaction feature 11, in particular exactly one interaction feature 11, is provided along the path between the initial position and the end position. When the piston rod 7 is moved from the initial position towards the end position, the respective interaction feature 11 mechanically cooperates with the blocking element 10. In particular, the respective interaction feature 11 slides along the blocking element 10. Due to mechanical cooperation of the blocking element 10 and the piston rod 7, in particular the interaction feature 11, backward movement of the piston rod 7 is prevented when the delivery operation is completed, which is described in detail on the following pages. In the following, the operation of setting and delivering a dose is described in detail:

For setting a dose of the drug 14, the dose member 5 is moved from a distal end position in the proximal direction with respect to the housing 3 to a proximal end position. Movement of the dose member 5 is transferred to the drive member 17 by mechanical cooperation of the dose member 5 and the drive member 17, e.g. via a rack and pinion mechanism. The drive member 17 is moved inside the piston rod 7 in the proximal direction with respect to the piston rod 7. Thereby, the flexible arm 18 of the drive member 17 slides along the indentations 32 arranged along the inner surface of the piston rod 7. Movement of the piston rod 7 in the proximal direction during the dose setting operation is prevented due to mechanical cooperation of the piston rod 7 and the blocking element 10. In particular, the blocking element 10 mechanically cooperates with the respective interaction feature 11, in particular with the elevation 30 of this interaction feature 11, such that movement of the piston rod 7 in the dose setting direction is prevented. This is described later on in more detail.

For delivering the set dose, the dose button 6 and, thus, the dose member 5 are moved in the distal direction. Movement of the dose member 5 is transferred to the drive member 17 by mechanical cooperation of the dose member 6 and the drive member 17. Due to mechanical cooperation of the flexible arm 18 and the inner structure, i.e. the respective indentation 32, of the piston rod 7 movement of the drive member 17 in the distal direction is transferred into movement of the piston rod 7 in the distal direction. Thereby, the piston rod 7 is moved from the initial position with respect to the blocking element 10 to the end position with respect to the blocking element 10. When the piston rod 7 is moved in the distal direction, the interaction feature 11 slides along the blocking member 10. The blocking member 10 is, at first, brought into mechanical cooperation with the elevation 30. Thereby, the blocking member 10 is deflected in the radial outward direction. Then, upon further movement of the piston rod 7 towards the end position, the blocking member 10 passes from the elevation 30 into the indentation 31 of the interaction feature 11. Mechanical cooperation of the interaction feature 11 and the blocking member 10 is described in detail in connection with FIGS. 3 and 4.

When the blocking member 10 passes from the elevation 30 into the indentation 31, an operating noise is provided to the user. In particular, when the blocking member 10 passes from the elevation 30 to the indentation 31, the radially outwardly deflected blocking member 10 relaxes such that the blocking member 10 gets into mechanical cooperation with the indentation 31. The operating noise is generated when the blocking member 10 gets into abutment with the indentation 31.

However, when the operating noise is provided, the piston rod 7 is not yet positioned in the end position. This is due to mechanical tolerances necessary during manufacturing and assembly of the device 1. The necessary tolerances make it impossible to place the operating noise exactly at the end of a dose delivery operation. In addition, room for a back-off movement has to be provided, as described below. For positioning the piston rod 7 in the end position, i.e. for delivering the complete dose, the dose button 6 must be moved further in the distal direction beyond the starting position with respect to the housing 3. Accordingly, the piston rod 7 is driven further distally with respect to the blocking member 10. Thereby, the indentation 31 slides along the blocking member 10. When the complete dose was dispensed, the dose button 6 is arranged in its most distal position. A back-off mechanism, e.g. a spring, now pushes the piston rod 7 and, thus, the bung 8 slightly in the proximal direction such that the piston rod 6 is arranged in the end position with respect to the blocking member 10 and such that the button 6 is arranged in the starting position with respect to the housing 3. When the piston rod 7 is in the end position, it is arranged at distance from the elevation 30. Due to the back-off mechanism it is prevented that the piston rod 7 exerts a force onto the bung 8 after completing the delivery operation, which could lead to droplets, for example.

For more details concerning the operation of the device 1, it is referred to documents WO 2008/058666 A1 and WO 2008/058668 A1 which references a similar device.

As mentioned above, when the interaction feature 11 mechanically cooperates with the blocking element 10 an operating noise is provided to the user. The operating noise may be an audible and/or tactile feedback, like a noise and/or a vibration. The operating noise may be a detent noise, for example. The operating noise is provided to the user before the dose delivery operation is completed, in particular before the piston rod 7 and, thus, the interaction feature 11, is positioned in the end position with respect to the blocking element 10.

The interaction feature 11 may be designed to homogenize the operating noise. In this way, it may be prevented that the user interprets the operating noise as signalling the end of the dose delivery operation. In such a case, the user would interrupt the dose delivery operation. In particular, the user would stop pushing onto the dose button 6 for moving the piston rod 7 in the dose delivery direction and, thus, into the end position respect to the blocking element 10, before the complete dose was delivered.

For avoiding that the user interprets the operating noise as signalling the end of the dose delivery operation, the interaction feature 11 may be designed in a special fashion, for example as described in the following text:

A) In one embodiment (see FIG. 3) the respective interaction feature 11 comprises exactly one elevation 30 and exactly one indentation 31. The elevation 30 comprises a first, i.e. distal, section 20A. The elevation 30 comprises a second, i.e. proximal, section 20B. The first section 20A is that section with which the blocking element 10 mechanically cooperates at first when the piston rod 7 is moved from the initial position towards the end position with respect to the blocking element 10.

The distal section 20A is oblique with respect to the main longitudinal axis x of the piston rod 7. The proximal section 20B is less oblique than the distal section. The outer surface of the first and second section 20A, 20B is smooth. This may help to homogenize, e.g. to reduce, the operating noise which is generated when the blocking element 10 mechanically cooperates with the first and second section 20A, 20B during the delivery operation. In particular, the outer surface of the elevation 30 is so smooth that an operating noise is provided only when the blocking element 10 passes from the elevation 30 into the indentation 31 during movement of the piston rod 7 towards the end position.

During the delivery operation, the piston rod 7 is moved from the initial position to the end position as described above. Thereby, at first, the distal section 20A is brought into mechanical cooperation with the blocking element 10. In particular, the distal section 20A slides along the blocking member 10. Thereby, the blocking member 10 is deflected in the radial outward direction with respect to the housing 3. When the piston rod 7 and, thus, the interaction feature 11 is moved further distally, the blocking element 10 passes over from the distal section 20A to the proximal section 20B. The blocking element 10 then slides down the proximal section 20B, thereby more and more relaxing in the radial inward direction with respect to the housing 3, when the piston rod 7 is further moved distally. Upon further movement of the piston rod 3, the blocking element 10 completely relaxes in the radial outward direction, passing from the second section 20B over into the indentation 10. When the blocking element 10 relaxes, the operating noise is provided to the user, as described above. When the piston rod 7 is in the end position, the blocking element 10 is arranged at a distance from the second section 20B and the dose delivery operation is completed.

If the user now moved the button 6 proximally, e.g. for setting a further dose or, if the user unintentionally pulled the button 6, the piston rod 7 can only be slightly moved in the proximal direction until the blocking element 10 comes into mechanical cooperation with the second section 20B. In other words, the piston rod 7 can be moved proximally only for a distance which corresponds to the distance between the blocking element 10 and the second section 20B after the dose delivery operation was completed. When the blocking element 10 and the second section 20B mechanically cooperate, the piston rod 7 is prevented from being displaceable in the direction opposite to the dose delivery direction, i.e. the dose setting direction. In other words, the blocking element 10 and the elevation 30 are arranged to prevent movement of the piston rod 7 in the dose setting direction.

A height difference between the elevation 30 and the indentation 31 may be greater than 0.1 mm. Preferably, the height difference is smaller than 0.3 mm. Preferably, the height difference amounts to 0.2 mm. The height difference between the elevation 30 and the indentation 31 may be between 0.1 mm and 0.3 mm.

The height difference between the elevation 30 and the indentation 31 is smaller than the height difference between an elevation and an indentation of an interaction feature 11 known from the prior art (see FIG. 5). In the prior art, the height difference between the elevation and the indentation known from the prior art is greater than 0.3 mm. In the prior art, the height difference amounts to 0.5 mm, for example.

In other words, the height difference between the elevation 30 and the indentation 31 shown in FIG. 3 is reduced as compared to the height difference known from the prior art (FIG. 5). In this way, the operating noise which arises from mechanical cooperation of the interaction feature 11 and the blocking element 10, in particular which arises when the blocking element 10 passes from elevation 30 into the indentation 31, may be homogenized, e.g. minimized.

Moreover, in the prior art (FIG. 5), the indentation comprised an undercut 11B. This undercut 11B caused the blocking element 10 to snap from the elevation into the indentation. Thereby, an operating noise was created which was easy to be misinterpreted by the user as signalling the end of the delivery operation. As shown in FIG. 3, the indentation 31 does no longer comprise an undercut. Rather, the indentation 31 is sloped. In particular, there is a sloped transition of the blocking element 10 from the elevation into the indentation during the delivery operation. Abrupt changes in the height, which may lead to a distinct operating noise, may be prevented in this way when the blocking member 10 passes into the indentation. Rather, the blocking element 10 can slide down from the elevation 30 into the indentation 31. When the blocking element 10 slides down into the indentation 31 instead of snapping into the indentation 31, a reduced operating noise is provided. In particular, the blocking element 10 may slide into the indentation 31 without creating operating noise. In other words, due to this specific design of the indentation 31 the operating noise which arises when the blocking element 10 passes from elevation 30 into the indentation 31 may be homogenized, in particular minimized.

The operating noise may be minimized such that the user can almost not or no longer realize the operating noise generated by the mechanical cooperation of the interaction feature 11 and the blocking element 10.

Altogether, the features that the elevation 30, in particular the sections 20A, 20B, have a smooth outer surface, without any further structure which would generate a noticeable operating noise when the blocking element 10 passes this structure, and that the height difference between the elevation 30 and the indentation 31 is reduced have the effect that the user does no longer interpret the operating noise as signalling the end of the delivery operation so as to compared to the prior art device. Hence, the risk that the user interrupts the dose delivery operation due to a significant operating noise is minimized. In this way, a user friendly and safe drug delivery device 1 is provided.

Due to the reduced height difference between the elevation 30 and the indentation 31, the angle of the blocking element 10 with respect to the piston rod 7 may be reduced as compared to the design of the blocking element 10 known from the prior art (FIG. 5). This may have the advantage that a device 1 with a smaller outer dimension, in particular a smaller diameter, is provided.

B) In a further embodiment (see FIG. 4), the interaction feature 11 comprises a plurality of teeth. In particular, the interaction feature 11 comprises a plurality of elevations 22, 23 and indentations 31. In particular, the interaction feature 11 comprises two, three or more elevations 22, 23 and two, three or more indentations 31. The interaction feature 11 comprises one pair of an elevation 23 and an indentation 31 which is provided at last along the path between the initial position and the end position of the piston rod 7. This respective elevation 23 is in the following referred to as the last or proximal elevation 23. The last elevation 23 may be a saw tooth. The respective indentation 31 is in the following referred to as the last or proximal indentation 31. The last elevation 23 and the last indentation 31 are provided at last along the path between the initial position and the end position of the piston rod 7 with respect to the blocking element 10. The interaction feature 11 comprises one, two or more elevations 22 and indentations 31 which are arranged more distal as compared to the proximal elevation 23. These elevations 22 and indentations 21 are in the following referred to as distal elevations 22 and distal indentations 31. The length of the last indentation 31 as seen along the direction of movement of the piston rod 7 during dose delivery may be greater than the length of the respective distal indentation 31.

The respective elevation 22, 23 comprises a first, i.e. distal, section 22A, 23A and a second, i.e. proximal, section 22B, 23B. The respective first section 22A, 23A is that section with which the blocking element 10 mechanically cooperates at first as compared to the respective second section 22B, 23B when the piston rod 7 is moved from the initial position towards the end position. The respective first section 22A, 23A is oblique with respect to the main longitudinal axis of the piston rod 7. The respective second section 22B, 23B is less oblique than the respective first section 22A, 23B. The respective second section 22B, 23B may run perpendicularly with respect to the main longitudinal axis of the piston rod 7.

The axial distance d between two succeeding elevations 22, 23 belonging to the same interaction feature 11 is smaller than the distance D between the last elevation 23 of one interaction feature 11 and an elevation 22 belonging to a succeeding interaction feature with which the blocking element 10 would mechanically cooperating during a succeeding delivery operation.

The respective elevation 22, 23 arises from the outer surface of the piston rod 7 by 0.3 mm or more. In particular, the height difference between the respective elevation 22, 23 and an indentation 31 of the interaction feature 11 is greater than or equal to 0.3 mm. The height difference between the respective elevation 22, 23 and an indentation 31 of the interaction feature 11 may be smaller than or equal to 0.5 mm. For example, the height difference between the last elevation 23 and one indentation 31 arises to 0.5 mm. The height difference between the respective elevation 22, 23 and an indentation 31 of the interaction feature 11 may be between 0.3 mm and 0.5 mm, for example. The height difference between the last elevation 23 and one indentation 31 may be similar to the height difference between an elevation and an indentation of an interaction feature 11 known from the prior art (FIG. 5). The height difference between the last elevation 23 and one indentation 31 may be greater than the height difference between the one of the distal elevations 22 and one indentation 31. As an alternative (not shown in the Figures), the height difference between the last elevation 23 and one indentation 31 may be similar to, e.g. equal to, the height difference between the one of the distal elevations 22 and one indentation 31. The height difference between a distal elevation 22 and one indentation 31 may arise to 0.4 mm, for example.

For the mechanical cooperation of the blocking element 10 with the interaction feature 11, i.e. with the respective elevation 22, 23 and indentation 31 of the interaction feature 11, it is referred to embodiment A.

In this embodiment, however, the operating noise provided by mechanical cooperation of the plurality of elevations 22, 23 and indentations 31 and the blocking element 10 comprises a sequence of tactile and/or audible signals to the user. In particular, whenever the blocking element 10 passes from the respective elevation 22, 23 into the succeeding indentation 31, an operating noise is generated. Thereby, the operating noise which arises when the blocking element 10 passes from the last elevation 23 into the last indentation 31 is similar, preferably, equal to the operating noise which arises when the blocking element 10 passes from a distal elevation 22 into a distal indentation 31. In other words, all noises may be of equal volume, so that none is especially significant to the user which could lead to the user misinterpreting one of the noises as signaling the end of the delivery operation.

The outer surface of the respective elevation 22, 23 is smooth. This may help to homogenize, e.g. to reduce, the operating noise which is generated when the blocking element 10 mechanically cooperates with the interaction feature 11 during the delivery operation.

After dose delivery was completed, the blocking element 10 is arranged at a distance from the proximal section 23B of the last elevation 23 as described in connection with embodiment A. When the dose button 6 is now moved proximally, the piston rod 7 can only be slightly moved in the proximal direction until the blocking element 10 comes into mechanical cooperation with the second section 23B. When the blocking element 10 and the second section 23B mechanically cooperate, the piston rod 7 is prevented from being further displaceable in the dose setting operation.

Altogether, the features that the elevations 22, 23 have a smooth outer surface and that a sequence of operating noises is provided during the delivery operation have the effect that the operating noise is homogenized. Hence, the risk that the user interrupts the dose delivery operation is minimized as the user may interpret none of the noises as signalling the end of the dose delivery operation. In this way, a user friendly and safe drug delivery device 1 is provided.

Due to the increased number of elevations and indentations of the previously described interaction feature 11 in comparison to an interaction feature 11 known from the prior art (FIG. 5), the angle of the blocking element 10 with respect to the piston rod 7 must be steeper as compared to the design of the blocking element 10 known from the prior art. Otherwise, the blocking element 10 could not engage the respective elevation 22, 23 and indentation 31. This may have the advantage that a device 1 is provided which can be handled very easy due to a larger outer diameter of the device 1. This may especially useful for older users with diminished abilities to grab.

Of course, features of different embodiments described herein can be combined with one another to form further embodiments which were not described above. In particular, the embodiment, where a sequence of operating signals is provided (embodiment B) and the embodiment, where a minimized operating noise is provided (embodiment A), may be combined for different interaction features, for example.

The invention claimed is:
1. An assembly for a drug delivery device comprising
a blocking element and
a piston rod having an interaction feature which is adapted and arranged to mechanically cooperate with the blocking element,
wherein, for delivering a dose of a drug, the piston rod is arranged and configured to be moved from an initial position to an end position with respect to the blocking element, wherein the interaction feature is provided along a path between the initial position and the end position,
and wherein an operating noise is provided to a user when the interaction feature mechanically cooperates with the blocking element while moving the piston rod from the initial position to the end position for dose delivery, and
wherein the interaction feature is adapted to homogenize the operating noise so as to prevent the operating noise from being interpreted by the user as signaling an end of the dose delivery operation, wherein the interaction feature comprises only one elevation and only one indentation, and wherein the indentation is sloped in a proximal direction such that the blocking member can slide along the slope in the proximal direction from the elevation into the indentation while moving the piston rod from the initial position to the end position for dose delivery.

2. The assembly according to claim 1, wherein the operating noise is provided to the user before the piston rod is positioned in the end position with respect to the blocking element.

3. The assembly according to claim 1, wherein the interaction feature is provided along an outer surface of the piston rod.

4. The assembly according to claim 3, wherein the assembly comprises a plurality of interaction features, and wherein the elevations and the indentations of succeeding interaction features are arranged in an alternating fashion along the piston rod.

5. The assembly according to claim 4, wherein succeeding interaction features comprise an equal axial dimension, and wherein, for delivering a dose, only one of the interaction features mechanically cooperates with the blocking element.

6. The assembly according to claim 1, wherein the interaction feature is configured to prevent movement of the piston rod in a direction opposite to a dose delivery direction with respect to the blocking element by mechanical cooperation with the blocking element.

7. The assembly according to claim 1, wherein the elevation comprises a first section and a second section, wherein the first section is that section with which the blocking element mechanically cooperates at first when the piston rod is moved from the initial position towards the end position, wherein, when the piston rod is in the end position, the second section and the blocking element are arranged with respect to one another such that, when the blocking element and the second section mechanically cooperate with one another, the piston rod is prevented from being displaced in a direction opposite to a dose delivery direction.

8. The assembly according to claim 1, wherein an outer surface of the elevation is so smooth that an operating noise is provided only when the blocking element passes from the elevation to the indentation when the piston rod is moved towards the end position.

9. A drug delivery device comprising the assembly according to claim 1, wherein the device comprises a housing and a reservoir holding a plurality of doses of the drug, wherein the at least one blocking element is integrally formed with or is connected to the housing, and wherein the blocking element is secured against axial and rotational movement with respect to the housing.

10. The device according to claim 9, wherein the device is a fixed dose device.

11. The assembly according to claim 1, wherein a height difference between the elevation and the indentation is smaller than 0.3 millimeters (mm).

12. The assembly according to claim 11, wherein the height difference between the elevation and the indentation is greater than 0.1 mm.

13. An assembly for a drug delivery device comprising
a blocking element and
a piston rod having an interaction feature which is adapted and arranged to mechanically cooperate with the blocking element,
wherein, for delivering a dose of a drug, the piston rod is arranged and configured to be moved from an initial position to an end position with respect to the blocking element, wherein the interaction feature is provided along a path between the initial position and the end position,
and wherein an operating noise is provided to a user when the interaction feature mechanically cooperates with the blocking element while moving the piston rod from the initial position to the end position for dose delivery, and
wherein the interaction feature is adapted to homogenize the operating noise so as to prevent the operating noise from being interpreted by the user as signaling an end of a dose delivery operation,
wherein the interaction feature comprises a plurality of elevations and indentations, wherein the interaction feature comprises (i) one pair of elevation and indentation which is provided at last along the path between the initial position and the end position of the piston rod with respect to the blocking element and (ii) at least one other pair of elevation and indentation located distally relative to the last pair, wherein the blocking element in cooperation with each pair of elevation and indentation of the interaction feature generates an audible or tactile feedback, wherein the feedback provided by mechanical cooperation of the last pair of indentation and elevation and the blocking element is similar to the feedback provided by mechanical cooperation of the blocking element with each pair of the at least one other pair of elevation and indentation, wherein a height difference between the elevation and the indentation of the last pair is greater than a height difference between the elevation and the indentation of the at least one other pair.

14. The assembly according to claim 13, wherein an axial distance between two succeeding elevations of the interaction feature is smaller than the distance between the last elevation of the interaction feature and an elevation belonging to a succeeding interaction feature.

15. The assembly according to claim 13, wherein the height difference between the elevation and the indentation of the last pair is smaller than or equal to 0.5 millimeters (mm), and wherein the height difference between the elevation and the indentation of the at least one other pair is greater than or equal to 0.3 mm.

16. An assembly for a drug delivery device comprising
a blocking element and
a piston rod having an interaction feature which is adapted and arranged to mechanically cooperate with the blocking element,
wherein, for delivering a dose of a drug, the piston rod is arranged and configured to be moved from an initial position to an end position with respect to the blocking element, wherein the interaction feature is provided along a path between the initial position and the end position,
and wherein an operating noise is provided to a user when the interaction feature mechanically cooperates with the blocking element while moving the piston rod from the initial position to the end position for dose delivery, and
wherein the interaction feature is adapted to homogenize the operating noise so as to prevent the operating noise from being interpreted by the user as signaling an end of the dose delivery operation,
wherein the interaction feature comprises only one elevation and only one indentation,
wherein a height difference between the elevation and the indentation is smaller than 0.3 millimeters (mm), and
wherein the height difference between the elevation and the indentation is greater than 0.1 mm.

* * * * *